United States Patent [19]

Morrison

[11] Patent Number: 4,926,000

[45] Date of Patent: May 15, 1990

[54] BENZENE CONVERSION OVER ZSM-5

[75] Inventor: Roger A. Morrison, Deptford, N.J.

[73] Assignee: Mobil Oil Corporation, New York, N.Y.

[21] Appl. No.: 213,755

[22] Filed: Jun. 30, 1988

[51] Int. Cl.$^5$ .................................................. C07C 2/76
[52] U.S. Cl. .................................... 585/476; 585/410; 585/475
[58] Field of Search ................ 585/410, 467, 475, 476

[56] References Cited

U.S. PATENT DOCUMENTS

| | | | |
|---|---|---|---|
| 3,668,264 | 6/1972 | Alley ................................. | 585/476 X |
| 3,784,618 | 1/1974 | Suggitt et al. ................... | 585/476 X |
| 4,085,156 | 4/1978 | Frilette et al. .................. | 208/120 X |
| 4,157,950 | 6/1979 | Frilette et al. .................. | 585/476 X |

OTHER PUBLICATIONS

Journal of Catalysis, 4, 310–311, "Sorption and Catalytic Properties of Natural Mordenite", (1965).
B. Imelik et al. (Editors), Catalysis by Zeolites (1980); "Hydrocarbon Reactions Catalysed by Mordenites", pp. 151–159.

*Primary Examiner*—Patrick P. Garvin
*Assistant Examiner*—George R. Fourson
*Attorney, Agent, or Firm*—Alexander J. McKillop; Charles J. Speciale; Marina V. Schneller

[57] ABSTRACT

Benzene reacts with itself to produce liquid aromatic compounds having more than 6 carbon atoms, in the presence of zeolite characterized as a medium pore size and having an activity defined by an alpha value of at least 50.

49 Claims, No Drawings

BENZENE CONVERSION OVER ZSM-5

FIELD OF THE INVENTION

The invention relates to the conversion of benzene by reaction with itself to produce higher molecular weight products which are liquid at ambient conditions. The conversion is catalytically effected by a zeolite of the class of medium pore size zeolites, sometimes circumscribed by the description of Constraint Index of 1 to 12.

BACKGROUND OF THE INVENTION

Few studies have been undertaken on the conversion of benzene. One possible explanation is the presumption that benzene is stable over acid catalysts. Some early work disputed that art held presumption. Cf. Frilette, V. J., and Rubin, M. K. "Journal of Catalysis" 4, p. 310-311, 1965. Karge, H. G., and Ladebeck, J., "Studies in Surface Science and Catalysis", #5, Proceedings of the International Symposium, 1980.

Although in the past there has been little incentive for studying its conversion to other products because of the high value of benzene as a basic petrochemical, anticipation of environmental regulations in gasoline has provided the incentive.

Various benzene conversions have been proposed such as alkylation with olefins, alcohols, or olefinic fragments from paraffin cracking, and interaromatic conversions such as xylene transalkylation. The common feature of these benzene reduction schemes is the use of another reactant.

The conversion discussed herein is catalyzed by zeolites. Naturally occurring and synthetic zeolites have been demonstrated to exhibit catalytic properties for various types of hydrocarbon conversions. Certain zeolites are ordered porous crystalline aluminosilicates having definite crystalline structure as determined by X-ray diffraction studies. Such zeolites have pores of uniform size which are uniquely determined by unit structure of the crystal. The zeolites are referred to as "molecular sieves" because the uniform pore size of a zeolite material may allow it to selectively absorb molecules of certain dimensions and shapes.

By way of background, one authority has described the zeolites structurally, as "framework" auminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula

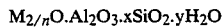

$$M_{2/n}O.Al_2O_3.xSiO_2.yH_2O$$

In the empirical formula, M was described therein to be sodium, potassium, magnesium, calcium, strontium and/or barium; x is equal to or greater than 2, since $AlO_4$ tetrahedra are joined only to $SiO_4$ tetrahedra, and n is the valence of the cation designated M; and the ratio of the total of silicon and aluminum atoms to oxygen atoms is 1:2. D. Breck, ZEOLITE MOLECULAR SIEVES, John Wiley & Sons, New York p. 5 (1974).

The prior art describes a variety of synthetic zeolites. These zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5, its X-ray diffraction pattern, and its preparation are described in U.S. Pat. No. 3,702,886, the entire disclosure of which is incorporated by reference herein; zeolite ZSM-11 (U.S. Pat. No. 3,709,979) and zeolite SZM-23 (U.S. Pat. No. 3,076,842), merely to name a few.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. patent application Ser. No. 373,451 filed Apr. 30, 1982, and now pending. The entire description thereof is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-57 is a zeolite, the X-ray diffraction pattern and synthesis of which are described in EP 0,174,121.

It is to be understood that by incorporating by reference the foregoing patents and patent applications to describe examples of specific members of the novel class with greater particularity, it is intended that identification of the therein disclosed crystalline zeolites by resolved on tha basis of their respective X-ray diffraction patterns. It is the crystal structure, as identified by the X-ray diffraction "fingerprint", which establishes the identity of the specific crystalline zeolite material. The crystal structure of known zeolites may include gallium, boron, iron and chromium as framework elements, without changing its identification by the X-ray diffraction "fingerprint"; and these gallium, boron, iron and chromium containing silicates and aluminosilicates may be useful, or even preferred, in some applications described herein.

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 Angstroms. On the other hand, zeolites which provide relatively free access to the internal zeolite structure have a low value for the Constraint Index, and usually pores of large size, e.g. greater than 8 Angstroms. The method by which Constraint Index is determined is described fully in U.S. Pat. No. 4,016,218, incorporated herein by reference for details of the method.

| | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

SUMMARY OF THE INVENTION

The invention relates to the catalytic reaction of benzene with iself to produce a mixture comprising primarily alkylbenzene and alkylnapthalenes, over a catalyst comprising a zeolite having a Constraint Index of 1 to 12. The catalyst allows for maintenance of high benzene conversion with reasonable aging rates as a consequence of a reduced tendency to form coke. In the absence of hydrogen minimal ring loss is observed, although aging rates are higher than when hydrogen is employed. Addition of hydrogen substantially reduces aging rate at the expense of increased selectivity to gas as a consequence of hydrocracking. The results obtained here represent a significant improvement over those obtained by Frilette and Rubin some 20 years ago with mordenite.

Application of the invention includes reduction of the benzene content of gasoline, and the preparation of petrochemical feedstocks.

DETAILED DESCRIPTION OF THE INVENTION

Catalytic conditions at which benzene reacts with itself include atemperature of 800°–1100° F.; a pressure of 100 to 1500 psig, preferably 300–800 psig, and a WHSV of 0.1 to 10 preferably 0.1 to 5. Hydrogen to hydrocarbon mole ratios ($H_2$/HC) can range up to 5:1 and preferably up to 2:1.

As noted above, the catalyst for the benzene conversion comprises a zeolite. The zeolite is one which is characterized by a Constraint Index of 1 to 12. Preferably, the zeolite is ZSM-5, ZSM-11, ZSM-22 or ZSM-57. The zeolite most preferred is ZSM-5. ZSM-5 is a zeolite the Constraint Index of which measured at different temperatures but within the bounds of conversion specified varies but remains within the range of 1 to 12. Cf. Frillette et al, J. CATAL., Vol. 67, No. 1, 218 at 220 (1981). Coke production, with these catalysts is limited, and catalyst deactivation by coking is accordingly substantially nil. Preferably, the zeolite has an aplha value of at least 50. The Alpha value is an approximate indication of the catalytic cracking activity of the catalyst compared to a reference standard amorphous silica-alumina catalyst and it gives the relative rate constant (rate of normal hexane conversion per volume of catalyst per unit time). It is based on the activity of a highly active silica-alumina cracking catalyst taken as an Alpha of 1 (Rate Constant=0.016 sec$^{-1}$). In the case of zeolite HZSM-5, only 174 ppm of tetrahedrally coordinated $Al_2O_3$ are required to provide an Alpha Value of 1. The Alpha Test is described in U.S. Pat. No. 3,354,078 and in The Journal of Catalysis, Vol. IV, pp. 552–529 (August 1965).

Tha catalytic reaction can be undertaken in the presence or absence of hydrogen; and thus the $H_2$/HC (feed) mole ratio can range from 0 to 5:1. Thus, the conversion does not require addition of hydrogen.

However, if hydrogen is present, it reduces condensed ring(s) production and facilitates hydrocracking to light gas and reduces aging. In the absence of hydrogen, the process of the invention is applicable to naphthalene and m-naphthalene production for petrochemical use.

EXAMPLES

The primary catalyst was H-ZSM-5 (one crystal dimension of which is at most 0.5 microns), $SiO_2/Al_2O_3=40$, 85% zeolite-15% $Al_2O_3$ binder, 1/16 inch extrudate, alpha=500. Also used were three experimental catalysts. The first was a ZSM-5 zeolite co-crystallized with 4.6% gallium which was used as binder-free 20×60 mesh particles, and had a $SiO_2/(Al_2O_3+Ga_2O_3)=42$ ($Al_2O_3=0.29\%$). The other catalysts were 1/16 inch extruded, 35% $Al_2O_3$ binder H-ZSM-4, $SiO_2/Al_2O_3=9$, and a similarly extruded H-ZSM-23, $SiO_2/Al_2O_3=114$, alpha=27. The catalysts were calcined in air at 900° F. prior to use.

Material balances were made by collection of the product stream in a liquid nitrogen-cooled trap and subsequent expansion of the gases into a precalibrated, constant volume glass system. Liquid and gas analysis were by GC. In some cases a large amount of condensed rings were generated. It is likely the methyl-naphthalenes indicated in the data tables include higher condensed ring systems which form on the external catalyst surface. Thus the methyl-naphthalenes and $C_{13}+$ analysis are approximate.

The data in Tables 1 and 2 show that the benzene does react over non-metallic H-ZSM-5. The main products are $C_7$-$C_8$ aromatics and naphthalenes as summarized below.

| Prod. Dist., Wt % | Wt % Conv. | | | Selectivity |
|---|---|---|---|---|
| | 26.8 | 53.8 | | |
| $C_1 + C_2$ | 0.2 | 0.6 | <—> | 1.1 |
| Benzene | 73.2 | 46.2 | | — |
| Toluene | 11.7 | 18.6 | | 34.6 |
| $C_8$ Ar | 1.7 | 2.9 | | 5.3 |
| $C_9$—$C_{12}$ Ar | 0.2 | 0.4 | | 0.9 |
| Naphthalene | 7.5 | 15.5 | | 28.9 |
| m-Naphthalenes | 5.6 | 13.7 | 25.4 | |
| $C_{13}+$ | — | 0.6 | | 3.9 |

The aromatic ring is stable and only a small amount is lost to cracked products. However, the ring is quite reactive converting to $C_7$-$C_8$ aromatics, condensed rings and coke. The latter two provide the hydrogen required to balance the stoichiometry. The pore size of ZSM-5 limits the growth of condensed rings permitting the products to leave the zeolite as liquid product. With larger pore materials which do not limit condensed ring growth, it is likely the reaction continues directly to coke resulting in rapid deactivation.

In the temperature range of 900°–950° F. and 1–2 WHSV, the conversion is substantial and there is probably little incentive to operate at higher temperatures which will accelerate coking. However, two other variables are important. First is pressure as seen below from Tables 1 and 2 at 945° F. and 1 WHSV.

| | Pressure, psig | | |
|---|---|---|---|
| | 100 | 500 | 800 |
| Selectivity | Wt % of Conv. | | |
| | 8.1 | 43.1 | 53.8 |
| $C_1$—$C_6$ | 1.9 | 1.5 | 1.1 |
| Toluene | 53.4 | 41.7 | 34.6 |
| $C_8$ Ar | 4.5 | 4.9 | 5.3 |
| $C_9$—$C_{12}$ Ar | 0.4 | 0.7 | 0.8 |
| Naphthalene | 24.6 | 28.9 | 28.9 |
| m-Naphthalenes | 14.0 | 20.1 | 25.4 |
| $C_{13}+$ | 1.2 | 2.3 | 3.9 |

The primary effect is on conversion which increases significantly with higher pressure. The selectivity also shifts from toluene to naphthalenes reflecting the pressure/conversion level changes.

TABLE 1

CONVERSION OF BENZENE OVER H-ZSM-5
(on matrix) $SiO_2/Al_2O_3=40$

| | | | |
|---|---|---|---|
| Temperature, °F. | 900.00 | 945.00 | 945.00 |
| Pressure, Psig | 800.00 | 800.00 | 800.00 |
| WHSV | 2.00 | 1.00 | 1.00 |
| $H_2.HC$ | 0.00 | 0.00 | 0.00 |
| Material Balance | 96.50 | 100.24 | 100.35 |
| Time on Stream. Hrs. | 5.30 | 5.70 | 24.70 |
| Product Dist., Wt % | | | |
| $C_1$ | 0.03 | 0.28 | 0.02 |
| $C_2$ | 0.12 | 0.31 | 0.14 |
| $C_2=$ | 0.00 | 0.00 | 0.00 |
| $C_3$ | 0.00 | 0.02 | 0.01 |
| $C_3=$ | 0.00 | 0.00 | 0.00 |
| ISO—$C_4$ | 0.00 | 0.00 | 0.00 |
| N—$C_4$ | 0.00 | 0.00 | 0.00 |
| $C_4=$ | 0.00 | 0.00 | 0.00 |
| ISO—$C_5$ | 0.00 | 0.00 | 0.00 |
| N—$C_5$ | 0.00 | 0.00 | 0.00 |
| $C_5=$ | 0.00 | 0.00 | 0.00 |
| 2.2 DM-$C_4$ | 0.00 | 0.00 | 0.00 |
| Cyclo-$C_5$ | 0.00 | 0.00 | 0.00 |
| 2,3 DM-$C_4$ | 0.00 | 0.00 | 0.00 |
| 2-M-$C_5$ | 0.00 | 0.00 | 0.00 |
| 3-M-$C_5$ | 0.00 | 0.00 | 0.00 |
| N—$C_6$ | 0.00 | 0.00 | 0.00 |
| $C_6=$ | 0.00 | 0.00 | 0.00 |
| M-Cyclo-$C_5$ | 0.00 | 0.00 | 0.00 |
| Benzene | 73.18 | 46.18 | 63.84 |
| Cyclo-$C_6$ | 0.00 | 0.00 | 0.00 |
| $C_7$'S | 0.00 | 0.00 | 0.00 |
| N—$C_7$ | 0.00 | 0.00 | 0.00 |
| Toluene | 11.71 | 18.60 | 14.10 |
| $C_8$'S | 0.00 | 0.00 | 0.00 |
| N—$C_8$ | 0.00 | 0.00 | 0.00 |
| $C_8$ Ar. | 1.65 | 2.87 | 1.61 |
| $C_9+$ Par. | 0.00 | 0.00 | 0.00 |
| $C_9$ Ar | 0.15 | 0.30 | 0.12 |
| $C_{10}$ Ar. | 0.07 | 0.14 | 0.10 |
| $C_{10}$—$C_{12}$ Ar. | 0.00 | 0.01 | 0.00 |
| Naphthalene | 7.52 | 15.53 | 11.52 |
| M-Naphthalenes* | ~5.57 | ~13.65 | ~7.92 |
| $C_{13}+$ 'S* | 0.00 | ~2.10 | ~0.61 |
| Total Wt % Conv. | 26.82 | 53.82 | 36.16 |
| Selectivity Wt % | | | |
| $C_1$—$C_3$ | 0.56 | 1.13 | 0.47 |
| $C_4$—$C_6$ | 0.00 | 0.00 | 0.00 |
| Toluene | 43.66 | 34.56 | 38.99 |
| $C_8$ Ar | 6.15 | 5.33 | 4.45 |
| $C_9$ Ar | 0.56 | 0.56 | 0.33 |
| $C_{10}$—$C_{12}$ Ar | 0.26 | 0.28 | 0.28 |
| Naphthalene | 28.04 | 28.86 | 31.86 |
| m-Napthalenes* | 20.77 | 25.36 | 21.90 |
| $C_{13}+$ 'S* | 0.00 | 3.90 | 1.69 |

*Condensed Aromatic Analysis Approximate.

The second important variable is hydrogen as seen in Table 2 and summarized below at 945° F., 500 psig, 1 WHSV.

| | | | | |
|---|---|---|---|---|
| $H_2/HC$ | 0 | | 2/1 | |
| Wt % Conversion | 43.1 | | 47.6 | |
| Product Dist., Wt % | | Selectivity | | Selectivity |
| $C_1$—$C_3$ | 0.6 | 1.5 | 8.0 | 16.8 |
| $C_4$—$C_6$ | — | — | 0.1 | 0.2 |
| Benzene | 57.0 | — | 52.4 | — |
| Toluene | 17.9 | 41.7 | 29.0 | 61.0 |
| $C_8$ Ar | 2.1 | 4.9 | 6.6 | 13.9 |
| $C_9$—$C_{12}$ Ar | 0.3 | 0.7 | 1.2 | 2.4 |
| Naphthalene | 12.5 | 28.9 | 1.1 | 2.3 |
| m-Naphthalenes | 8.7 | 20.1 | 1.6 | 3.3 |
| $C_{13}$+ | 1.0 | 2.3 | 0.1 | 0.2 |

With hydrogen, naphthalenes are dramatically reduced since condensed ring make is no longer required to maintain hydrogen stoichiometry. At the same time, ring hydrocracking becomes significant, producing more light gas. Reducing the pressure to 100 psig lowers conversion but selectivities are approximately equivalent.

TABLE 2

| CONVERSION OF BENZENE OVER H-ZSM-5 (on alumina) | | | | | |
|---|---|---|---|---|---|
| Temperature, °F. | 946.00 | 945.00 | 945.00 | 945.00 | 943.00 |
| Pressure, Psig | 100.00 | 500.00 | 500.00 | 100.00 | 800.00 |
| WHSV | 1.00 | 1.00 | 1.00 | 1.00 | 5.00 |
| $H_2.HC$ | 0.00 | 0.00 | 2/1 | 2/1 | 0.4/1 |
| Material Balance | 87.87 | 86.54 | 100.37 | 99.91 | 97.44 |
| Time on Stream. Hrs. | 5.70 | 5.70 | 5.30 | 5.30 | 4.50 |
| Product Dist., Wt % | | | | | |
| $C_1$ | 0.00 | 0.21 | 3.49 | 0.01 | 0.11 |
| $C_2$ | 0.06 | 0.36 | 3.28 | 0.24 | 0.16 |
| $C_2=$ | 0.01 | 0.01 | 0.02 | 0.03 | 0.01 |
| $C_3$ | 0.02 | 0.03 | 1.17 | 0.18 | 0.13 |
| $C_3=$ | 0.03 | 0.02 | 0.02 | 0.02 | 0.02 |
| ISO—$C_4$ | 0.03 | 0.01 | 0.05 | 0.02 | 0.01 |
| N—$C_4$ | 0.00 | 0.00 | 0.04 | 0.01 | 0.00 |
| $C_4=$ | 0.00 | 0.00 | 0.00 | 0.00 | 0.00 |
| ISO—$C_5$ | 0.00 | 0.00 | 0.00 | 0.00 | 0.00 |
| N—$C_5$ | 0.00 | 0.00 | 0.00 | 0.00 | 0.00 |
| $C_5=$ | 0.00 | 0.00 | 0.00 | 0.00 | 0.00 |
| 2.2 DM-$C_4$ | 0.00 | 0.00 | 0.00 | 0.00 | 0.00 |
| Cyclo-$C_5$ | 0.00 | 0.00 | 0.00 | 0.00 | 0.00 |
| 2,3 DM-$C_4$ | 0.00 | 0.00 | 0.00 | 0.00 | 0.00 |
| 2-M-$C_5$ | 0.00 | 0.00 | 0.00 | 0.00 | 0.00 |
| 3-M-$C_5$ | 0.00 | 0.00 | 0.00 | 0.00 | 0.00 |
| N—$C_6$ | 0.00 | 0.00 | 0.00 | 0.00 | 0.00 |
| $C_6=$ | 0.00 | 0.00 | 0.00 | 0.00 | 0.00 |
| M-Cyclo-$C_5$ | 0.00 | 0.00 | 0.00 | 0.00 | 0.00 |
| Benzene | 91.95 | 56.95 | 52.39 | 94.94 | 88.68 |
| Cyclo-$C_6$ | 0.00 | 0.00 | 0.00 | 0.00 | 0.00 |
| $C_7$'S | 0.00 | 0.00 | 0.00 | 0.00 | 0.00 |
| N—$C_7$ | 0.00 | 0.00 | 0.00 | 0.00 | 0.00 |
| Toluene | 4.30 | 17.94 | 29.02 | 3.02 | 6.70 |
| $C_8$'S | 0.00 | 0.00 | 0.00 | 0.00 | 0.00 |
| N—$C_8$ | 0.00 | 0.00 | 0.00 | 0.00 | 0.00 |
| $C_8$ Ar. | 0.36 | 2.09 | 6.63 | 0.93 | 2.06 |
| $C_9$ + Par. | 0.00 | 0.00 | 0.00 | 0.00 | 0.00 |
| $C_9$ Ar. | 0.02 | 0.18 | 1.04 | 0.09 | 0.14 |
| $C_{10}$ Ar. | 0.01 | 0.11 | 0.11 | 0.01 | 0.06 |
| $C_{10}$—$C_{12}$ Ar. | 0.00 | 0.01 | 0.00 | 0.00 | 0.00 |
| Naphthalene | 1.98 | 12.46 | 1.07 | 0.21 | 0.99 |
| M-Naphthalenes* | 1.13 | 8.66 | 1.56 | 0.29 | 0.89 |
| $C_{13}$ + 'S* | 0.10 | 0.97 | 0.10 | 0.01 | 0.05 |
| Total Wt % Conv. | 8.05 | 43.05 | 47.61 | 5.06 | 11.32 |
| Selectivity Wt % | | | | | |
| $C_1$—$C_3$ | 1.49 | 1.46 | 16.76 | 9.49 | 3.80 |
| $C_4$—$C_6$ | 0.37 | 0.02 | 0.19 | 0.59 | 0.09 |
| Toluene | 53.42 | 41.67 | 60.95 | 59.68 | 59.19 |
| $C_8$ Ar | 4.47 | 4.85 | 13.93 | 18.38 | 18.20 |
| $C_9$ Ar | 0.25 | 0.42 | 2.18 | 1.78 | 1.24 |
| $C_{10}$—$C_{12}$ Ar | 0.12 | 0.26 | 0.23 | 0.20 | 0.53 |
| Naphthalene | 24.60 | 28.94 | 2.25 | 4.15 | 8.75 |
| m-Naphthalenes* | 14.04 | 20.12 | 3.28 | 5.73 | 7.86 |
| $C_{13}$ + 'S* | 1.24 | 2.25 | 0.21 | 0.20 | 0.44 |

*M-Naphthalene and $C_{13}$ + 'S Analysis Approximated.

Table 3 shows a brief aging run at 925° F., 800 psig, 1 WHSV and 2/1 $H_2$/HC. At 60–65% conversion the aging rate is about 1.8° F./day permitting cycles of 1–2 months at these conditions.

TABLE 3

| BENZENE CONVERSION AND AGING OVER H-ZSM-5 (on alumina) WITH HYDROGEN | | | | | | | | |
|---|---|---|---|---|---|---|---|---|
| Temperature, °F. | 924.00 | 924.00 | 924.00 | 923.00 | 923.00 | 923.00 | 924.00 | 949.00 |
| Pressure, Psig | 800.00 | 800.00 | 800.00 | 800.00 | 800.00 | 800.00 | 800.00 | 800.00 |
| WHSV | 1.00 | 1.00 | 1.00 | 1.00 | 1.00 | 1.00 | 1.00 | 1.00 |
| $H_2.HC$ | 2.10 | 2.10 | 2.10 | 2.10 | 2.10 | 2.10 | 2.10 | 2.10 |
| Material Balance | 101.31 | 102.69 | 103.30 | 103.21 | 101.58 | 101.43 | 103.35 | 104.08 |
| Time on Stream-Hrs. | 5.00 | 29.00 | 53.00 | 77.00 | 101.00 | 173.00 | 193.00 | 217.00 |
| Product Dist., Wt % | | | | | | | | |
| $C_1$ | 6.96 | 8.61 | 7.50 | 7.27 | 7.46 | 6.23 | 6.98 | 10.41 |
| $C_2$ | 6.11 | 7.36 | 6.36 | 6.77 | 7.00 | 5.93 | 5.98 | 9.44 |
| $C_2=$ | 0.00 | 0.00 | 0.00 | 0.00 | 0.00 | 0.00 | 0.00 | 0.00 |
| $C_3$ | 1.34 | 1.36 | 1.36 | 1.49 | 1.62 | 1.57 | 1.58 | 1.25 |
| Benzene | 38.01 | 34.04 | 36.49 | 35.76 | 35.68 | 39.37 | 38.99 | 28.68 |
| Cyclo-$C_6$ | 0.00 | 0.00 | 0.00 | 0.00 | 0.00 | 0.00 | 0.00 | 0.00 |
| $C_7$'S | 0.00 | 0.00 | 0.01 | 0.01 | 0.00 | 0.00 | 0.00 | 0.00 |
| N-$C_7$ | 0.00 | 0.00 | 0.00 | 0.00 | 0.00 | 0.00 | 0.00 | 0.00 |
| Toluene | 31.84 | 31.60 | 31.91 | 32.09 | 31.97 | 31.86 | 31.20 | 31.13 |
| $C_8$'S | 0.00 | 0.00 | 0.00 | 0.00 | 0.00 | 0.00 | 0.00 | 0.00 |
| N-$C_8$ | 0.00 | 0.00 | 0.00 | 0.00 | 0.00 | 0.00 | 0.00 | 0.00 |
| $C_8$ Ar. | 9.36 | 10.01 | 9.60 | 10.01 | 10.01 | 9.46 | 9.21 | 11.47 |
| $C_9$+ Par. | 0.00 | 0.00 | 0.00 | 0.00 | 0.00 | 0.00 | 0.00 | 0.00 |
| $C_9$ Ar. | 1.51 | 1.64 | 1.45 | 1.55 | 1.56 | 1.56 | 3.12 | 1.89 |
| $C_{10}$ Ar. | 0.22 | 0.23 | 0.31 | 0.34 | 0.34 | 0.23 | 0.26 | 0.34 |
| $C_{10}$-$C_{12}$ Ar. | 0.01 | 0.01 | 0.01 | 0.01 | 0.00 | 0.01 | 0.02 | 0.02 |
| Naphthalene | 1.73 | 1.93 | 1.96 | 1.78 | 1.64 | 1.44 | 1.41 | 1.88 |
| M-Naphthalenes* | 2.73 | 3.06 | 2.91 | 2.80 | 2.63 | 2.26 | 2.16 | 3.35 |
| $C_{13}$+'S* | 0.15 | 0.12 | 0.09 | 0.07 | 0.03 | 0.03 | 0.03 | 0.09 |
| Total Wt % Conv. | 61.99 | 65.96 | 63.51 | 64.24 | 64.32 | 60.63 | 61.01 | 71.32 |
| Selectivity Wt % | | | | | | | | |
| $C_1$-$C_3$ | 23.25 | 26.27 | 23.96 | 24.17 | 25.00 | 22.60 | 22.19 | 29.58 |
| $C_4$-$C_6$ | 0.05 | 0.08 | 0.05 | 0.09 | 0.09 | 0.10 | 0.10 | 0.04 |
| Toluene | 51.36 | 47.91 | 50.24 | 49.95 | 49.70 | 52.55 | 51.14 | 43.65 |
| $C_8$ Ar | 15.10 | 15.18 | 15.12 | 15.58 | 15.56 | 15.60 | 15.10 | 16.08 |
| $C_9$ Ar | 2.44 | 2.49 | 2.28 | 2.41 | 2.43 | 2.57 | 5.11 | 2.65 |

TABLE 3-continued

| | BENZENE CONVERSION AND AGING OVER H-ZSM-5 (on alumina) WITH HYDROGEN | | | | | | | |
|---|---|---|---|---|---|---|---|---|
| $C_{10}-C_{12}$ Ar | 0.37 | 0.36 | 0.50 | 0.54 | 0.53 | 0.40 | 0.46 | 0.50 |
| Naphthalene | 2.79 | 2.93 | 3.09 | 2.77 | 2.55 | 2.38 | 2.31 | 2.64 |
| m-Napthalenes* | 4.40 | 4.64 | 4.58 | 4.36 | 4.09 | 3.73 | 3.54 | 4.70 |
| $C_{13}+$'S* | 0.24 | 0.18 | 0.14 | 0.11 | 0.05 | 0.05 | 0.05 | 0.13 |

*M-Naphthalenes and $C_{13}+$'S Analysis Approximate.

Table 4 shows results without hydrogen. As expected, aging is more severe because of the condensed ring make which facilitates coking. The aging rate is 5°–10° F./day at the 25% conversion level. By limiting conversion to this level it may be possible to obtain 1–2 week cycles operating in a swing reactor system.

TABLE 4

| BENZENE CONVERSION AND AGING OVER H-ZSM-5 (on alumina). NO $H_2$. | | | |
|---|---|---|---|
| Temperature, °F. | 923.00 | 925.00 | 925.00 |
| Pressure, Psig | 800.00 | 800.00 | 800.00 |
| WHSV | 1.00 | 1.00 | 1.00 |
| $H_2$.HC | 0.00 | 0.00 | 0.00 |
| Material Balance | 94.46 | 99.12 | 96.18 |
| Time on Stream. Hrs. | 5.30 | 48.80 | 72.30 |
| Product Dist., Wt % | | | |
| $C_1$ | 0.22 | 0.00 | 0.00 |
| $C_2$ | 0.31 | 0.06 | 0.02 |
| Benzene | 44.64 | 74.40 | 77.72 |
| Cyclo-$C_6$ | 0.00 | 0.00 | 0.00 |
| $C_7$'S | 0.00 | 0.00 | 0.00 |
| N—$C_7$ | 0.00 | 0.00 | 0.00 |
| Toluene | 19.91 | 10.33 | 9.16 |
| $C_8$'S | 0.00 | 0.00 | 0.00 |
| N—$C_8$ | 0.00 | 0.00 | 0.00 |
| $C_8$ Ar. | 3.19 | 1.30 | 1.21 |
| $C_9$ + Par. | 0.00 | 0.00 | 0.00 |
| $C_9$ Ar. | 0.36 | 0.09 | 0.06 |
| $C_{10}$ Ar. | 0.16 | 0.07 | 0.06 |
| $C_{10}$—$C_{12}$ Ar. | 0.01 | 0.00 | 0.00 |
| Naphthalene | 15.34 | 8.21 | 7.15 |
| M-Naphthalenes* | 13.98 | 5.26 | 4.42 |
| $C_{13}$ + 'S* | 1.87 | 0.28 | 0.20 |
| Total Wt % Conv. | 55.36 | 25.60 | 22.28 |
| Selectivity Wt % | | | |
| $C_1$—$C_3$ | 0.99 | 0.23 | 0.09 |
| $C_4$—$C_6$ | 0.00 | 0.00 | 0.00 |
| Toluene | 35.96 | 40.35 | 41.11 |
| $C_8$ Ar | 5.76 | 5.08 | 5.43 |
| $C_9$ Ar | 0.65 | 0.35 | 0.27 |
| $C_{10}$—$C_{12}$ Ar | 0.31 | 0.27 | 0.27 |
| Naphthalene | 27.71 | 32.07 | 32.09 |
| m-Naphthalenes* | 25.25 | 20.55 | 19.84 |
| $C_{13}$ + 'S* | 3.38 | 1.09 | 0.90 |

*M-Naphthalenes and $C_{13}$ + 's Analysis Approximate.

Table 5 shows the results with [Ga]-ZSM-5. This catalyst does not respond to temperature and has low activity. Ga is known to promote aromatization which accounts for the increase in condensed rings and probably subsequent coking. Potentially it seems metals could facilitate this reaction by increasing the molecular hydrogen make thus reducing the need for condensed ring make. However, hydrogen make is favored at low pressure which is contrary to the requirement of higher pressure for benzene conversion.

TABLE 5

| CONVERSION OF BENZENE OVER [Ga]-ZSM-5 (on alumina) | | |
|---|---|---|
| Temperature, °F. | 900.00 | 953.00 |
| Pressure, Psig | 800.00 | 800.00 |
| WHSV | 2.00 | 1.10 |
| $H_2$.HC | 0.00 | 0.00 |
| Material Balance | 103.22 | 92.96 |
| Time on Stream. Hrs. | 5.40 | 5.70 |

TABLE 5-continued

| CONVERSION OF BENZENE OVER [Ga]-ZSM-5 (on alumina) | | |
|---|---|---|
| Product Dist., Wt % | | |
| $C_1$ | 0.01 | 0.01 |
| $C_2$ | 0.02 | 0.03 |
| $C_2$= | 0.00 | 0.00 |
| $C_3$ | 0.03 | 0.02 |
| $C_3$= | 0.00 | 0.01 |
| ISO—$C_4$ | 0.01 | 0.02 |
| N—$C_4$ | 0.03 | 0.00 |
| Benzene | 95.39 | 91.52 |
| Cyclo-$C_6$ | 0.00 | 0.00 |
| $C_7$'S | 0.00 | 0.00 |
| N—$C_7$ | 0.00 | 0.00 |
| Toluene | 1.34 | 3.35 |
| $C_8$'S | 0.00 | 0.00 |
| N—$C_8$ | 0.00 | 0.00 |
| $C_8$ Ar. | 0.22 | 0.10 |
| $C_9$ + Par. | 0.00 | 0.00 |
| $C_9$ Ar. | 0.04 | 0.04 |
| $C_{10}$ Ar. | 0.04 | 0.05 |
| $C_{10}$—$C_{12}$ Ar. | 0.13 | 0.00 |
| Naphthalene | 0.49 | 0.93 |
| M-Naphthalenes* | ~1.89 | ~3.36 |
| $C_{13}$ + 'S* | ~0.36 | ~0.57 |
| Total Wt % Conv. | 4.61 | 8.48 |
| Selectivity Wt % | | |
| $C_1$—$C_3$ | 1.30 | 0.71 |
| $C_4$—$C_6$ | 0.87 | 0.12 |
| Toluene | 29.07 | 39.50 |
| $C_8$ Ar | 4.77 | 1.18 |
| $C_9$ Ar | 0.87 | 0.47 |
| $C_{10}$—$C_{12}$ Ar | 3.69 | 0.59 |
| Naphthalene | 10.63 | 10.97 |
| ~m-Naphthalenes* | 41.00 | 39.62 |
| ~$C_{13}$ + 'S* | 7.81 | 6.72 |

*m-Naphthalene and $C_{13}$ + 's aromatic analysis approximate.

Two runs were made with a slightly more constrained zeolite, ZSM-23, Table 6, and a larger pore zeolite, ZSM-4, Table 7. Neither catalyst gave more than 1–2% conversion which is close to the thermal background. The ZSM-23 probably lacks sufficient activity to catalyze this reaction (alpha=27) and its unidimensional pore structure will tend toward rapid deactivation. ZSM-4 should have sufficient activity but probably the larger pore material will coke rapidly resulting in no long term activity for this reaction. This is in line with published data which show that conversion over mordenite decreases from 5% to less than 1% in less than 1.5 hours at atmospheric pressure (2). High pressures may favor even faster deactivation.

TABLE 6

| BENZENE CONVERSION OVER H-ZSM-23 | |
|---|---|
| Temperature, °F. | 951.00 |
| Pressure, Psig | 800.00 |
| WHSV | 1.00 |
| $H_2$.HC | 0.00 |
| Material Balance | 89.36 |
| Time on Stream. Hrs. | 3.50 |
| Product Dist., Wt % | |
| $C_1$ | 0.00 |
| $C_2$ | 0.00 |
| $C_2$= | 0.00 |
| $C_3$ | 0.00 |

TABLE 6-continued

BENZENE CONVERSION OVER H-ZSM-23

| | |
|---|---|
| $C_3=$ | 0.00 |
| ISO—$C_4$ | 0.00 |
| Benzene | 98.55 |
| Cyclo-$C_6$ | 0.00 |
| $C_7$'S | 0.00 |
| N—$C_7$ | 0.00 |
| Toluene | 0.41 |
| $C_8$'S | 0.00 |
| N—$C_8$ | 0.00 |
| $C_8$ Ar. | 0.24 |
| $C_9$ + Par. | 0.00 |
| $C_9$ Ar. | 0.02 |
| $C_{10}$ Ar. | 0.02 |
| $C_{10}$—$C_{12}$ Ar. | 0.02 |
| Naphthalene | 0.22 |
| M-Naphthalenes* | 0.48 |
| $C_{13}$ + 'S* | 0.03 |
| Total Wt % Conv. | 1.45 |
| Selectivity Wt % | 0.00 |
| $C_1$—$C_3$ | 0.00 |
| $C_4$—$C_6$ | 0.00 |
| Toluene | 28.28 |
| $C_8$ Ar | 16.55 |
| $C_9$ Ar | 1.38 |
| $C_{10}$—$C_{12}$ Ar | 2.76 |
| Naphthalene | 15.17 |
| m-Naphthalenes* | 33.10 |
| $C_{13}$ + 'S* | 2.07 |

*M-Naphthalenes and $C_{13}$ + 'S Analysis Approximate.

TABLE 7

BENZENE CONVERSION OVER H-ZSM-4

| | |
|---|---|
| Temperature, °F. | 944.00 |
| Pressure, Psig | 800.00 |
| WHSV | 1.00 |
| $H_2$.HC | 0.00 |
| Material Balance | 93.62 |
| Time on Stream. Hrs. | 5.90 |
| Product Dist., Wt % | |
| $C_1$ | 0.00 |
| $C_2$ | 0.00 |
| $C_2=$ | 0.00 |
| $C_3$ | 0.00 |
| $C_3=$ | 0.00 |
| ISO—$C_4$ | 0.03 |
| Benzene | 98.70 |
| Cyclo-$C_6$ | 0.00 |
| $C_7$'S | 0.01 |
| N—$C_7$ | 0.00 |
| Toluene | 0.36 |
| $C_8$'S | 0.00 |
| N—$C_8$ | 0.00 |
| $C_8$ Ar. | 0.15 |
| $C_9$ + Par. | 0.00 |
| $C_9$ Ar. | 0.02 |
| $C_{10}$ Ar. | 0.00 |
| $C_{10}$—$C_{12}$ Ar. | 0.02 |
| Naphthalene | 0.23 |
| M-Naphthalenes* | 0.39 |
| $C_{13}$ + 'S* | 0.06 |
| Total Wt % Conv. | 1.30 |
| Selectivity Wt % | |
| $C_1$—$C_3$ | 0.00 |
| $C_4$—$C_6$ | 4.62 |
| Toluene | 27.69 |
| $C_8$ Ar | 11.54 |
| $C_9$ Ar | 1.54 |
| $C_{10}$—$C_{12}$ Ar | 1.54 |
| Naphthalene | 17.69 |
| m-Naphthalenes* | 30.00 |
| $C_{13}$ + 'S* | 4.62 |

*M-Naphthalenes and $C_{13}$ + 'S Analysis Approximate.

What is claimed is:

1. A process for converting benzene to a product comprising alkylbenzenes, alkylnaphthalenes and admixtures thereof, comprising reacting benzene with itself, in the presence of a catalyst composition comprising a zeolite, said zeolite exhibiting a Constraint Index of 1 to 12 and an alpha value of at least 50, by passing benzene over said catalyst at a temperature of 800°–1100° F., a pressure of 100–1500 psig, and a weight hourly space velocity of 0.1 to 5 WHSV; and recovering product.

2. The process of claim 1, wherein the zeolite is in its acid form.

3. The process of claim 2, wherein the zeolite is ZSM-5.

4. The process of claim 1, wherein the temperature ranges from 800 to about 950° F.

5. The process of claim 4, wherein the zeolite is ZSM-5.

6. The process of claim 1, wherein the zeoite is ZSM-5, ZSM-11, ZSM-22 or ZSM-57.

7. The process of claim 6, wherein the zeolite is ZSM-5.

8. The process of claim 1, undertaken in the absence of added hydrogen.

9. The process of claim 1, undertaken in the presence of hydrogen.

10. The process of claim 1, wherein the product includes compounds which are liquids at ambient conditions.

11. The process of claim 1, wherein the product comprises $C_7$ to $C_9$ aromatics.

12. The process of claim 1, wherein the product comprises $C_7$–$C_8$ aromatics.

13. The process of claim 1, wherein the product includes naphthalene.

14. The process of claim 1, wherein the pressure is greater than 300 psig.

15. The process of claim 1, wherein hydrogen is introduced to said conversion wherein the selectivity of the process for naphthalene is decreased.

16. The process of claim 15, wherein the hydrogen to benzene mole ratio is up to 5:1.

17. The process of claim 16, wherein said hydrogen to benzene mole ratio is up to 2:1.

18. A process for producing aromatic products having more than 6 carbon atoms which are liquids at ambient conditions, comprising contacting benzene with ZSM-5, said ZSM-5 being in its acid form, at a temperature of 800 to 1100° F., at a pressure of 100 to 1500 psig, at a WHSV of 0.1 to 5, and producing said products.

19. The process of claim 18, which further includes feeding hydrogen to said contacting.

20. The process of claim 19 wherein the hydrogen to benzene mole ratio ranges from greater than 0 to 5:1.

21. The process of claim 20, wherein the mole ratio is up to 2:1.

22. The process of claim 18, wherein the pressure is at least 300 psig.

23. The process of claim 18, wherein the pressure ranges from about 300 to about 800 psig.

24. The process of claim 18, wherein the temperature ranges up to 950° F.

25. The process of claim 24, wherein the pressure is at least 300 spig.

26. The process of claim 24, wherein the pressure ranges from about 300 to about 800 psig.

27. A process for reacting benzene with itself, comprising contacting benzene with a catalyst composition comprising a zeolite, said zeolite exhibiting a constraint index of 1 to 12 and an alpha value of at least 50, at a temperature of 800°–1100° F., a pressure of 100–1500 psig, and a weight hourly space velocity (WHSV) of 0.1 to 5 WHSV; and recovering naphthalene and meta-alkyl naphthalene.

28. The process of claim 27, wherein the zeolite is in its acid form.

29. The process of claim 28, wherein the zeolite is ZSM-5.

30. The process of claim 27, wherein the temperature ranges from 800° to about 950° F.

31. The process of claim 30, wherein the zeolite is ZSM-5.

32. The process of claim 27, wherein the zeolite is ZSM-5, ZSM-11, ZSM-22 or ZSM-57.

33. The process of claim 32, wherein the zeolite is ZSM-5.

34. The process of claim 27, undertaken in the absence of added hydrogen.

35. The process of claim 27, undertaken in the presence of hydrogen.

36. The process of claim 27, wherein product of the process further includes compounds which are liquids at ambient conditions.

37. The process of claim 27, wherein the product further comprises $C_7$ to $C_9$ aromatics.

38. The process of claim 27, wherein the product further comprises $C_7$–$C_8$ aromatics.

39. The process of claim 27, wherein the pressure is greater than 300 psig.

40. The process of claim 27, wherein hydrogen is co-fed during said contacting wherein the selectivity of the process for naphthalene is decreased.

41. The process of claim 40, wherein the hydrogen to benzene mole ratio is up to 5:1.

42. The process of claim 41, wherein said hydrogen to benzene mole ratio is up to 2:1.

43. The process of claim 42, wherein the pressure is at least 300 psig.

44. The process of claim 27, wherein the pressure ranges from about 300 to about 800 psig.

45. The process of claim 44, wherein the hydrogen to benzene mole ratio ranges from greater than 0 to 5:1.

46. The process of claim 45, wherein the mole ratio is up to 2:1.

47. The process of claim 27, wherein the temperature ranges up to 950° F.

48. The process of claim 47, wherein the pressure is at least 300 psig.

49. The process of claim 47, wherein the pressure ranges from about 300 to about 800 psig.

* * * * *